United States Patent [19]

Fedorov et al.

[11] Patent Number: 4,534,348
[45] Date of Patent: Aug. 13, 1985

[54] INSTRUMENT FOR MAKING CORNEAL INCISIONS

[75] Inventors: Svyatoslav N. Fedorov; Evgeny I. Degtev; Vladimir N. Golubev; Sergei V. Khromov; Igor A. Yatsenko; Alexandr A. Karavaev; Vladimir M. Yakushev, all of Moscow, U.S.S.R.

[73] Assignee: Moskovsky Nauchno-Issledovatelsky Institut Mirrokhirurgii Glaza, Moscow, U.S.S.R.

[21] Appl. No.: 456,985

[22] Filed: Jan. 10, 1983

Related U.S. Application Data

[63] Continuation-in-part of Ser. No. 375,272, Apr. 21, 1982.

[30] Foreign Application Priority Data

Jan. 12, 1982 [SU]  U.S.S.R. ............................. 3383704

[51] Int. Cl.³ ..................... A61B 17/32; B26B 1/08
[52] U.S. Cl. ................................... 128/305; 30/320; 30/338
[58] Field of Search .................. 30/329-333, 30/337-338, 293, 314, 317, 320-321, 339; 128/305, 314, 310

[56] References Cited

U.S. PATENT DOCUMENTS

| | | | |
|---|---|---|---|
| 477,817 | 6/1892 | Nielsen | 30/330 |
| 1,813,723 | 7/1931 | Beaver | 30/329 |
| 1,940,855 | 12/1933 | Friedman | 30/337 |
| 2,250,237 | 7/1941 | Schwartzkopf | 30/332 |
| 2,684,026 | 7/1954 | Randolph, Sr. | 30/329 |
| 3,076,263 | 2/1963 | Musto | 30/317 |
| 3,845,554 | 11/1974 | Joanis et al. | 30/330 |
| 3,922,784 | 12/1975 | Prince et al. | 30/329 |
| 3,967,377 | 7/1976 | Wells | 30/338 |
| 3,977,077 | 8/1976 | Rebold | 30/317 |

Primary Examiner—John D. Yasko
Assistant Examiner—Gene B. Kartchner
Attorney, Agent, or Firm—Fleit, Jacobson, Cohn & Price

[57] ABSTRACT

The invention generally relates to medicine, but more particularly, to an instrument for making corneal incisions useful, for example, in the surgical treatment of myopia.

The instrument disclosed herein includes a case, a holder of a cutting member being mounted within the case for reciprocation relative thereto. The holder is provided with a lock member for a cutting member at one end thereof, its opposite end accommodating a stem engaging a screwnut type drive urging said holder into motion. A stop is mounted on the case anteriorly relative to said holder. According to the invention, the portion of the holder facing the stop which is rectangular in cross-section, is preferably provided with a rectangularly fashioned groove along with a lever clip mounted therein, to secure the cutting member in position.

5 Claims, 5 Drawing Figures

INSTRUMENT FOR MAKING CORNEAL INCISIONS

This application is a continuation-in-part of U.S. application Ser. No. 375,272 filed Apr. 21, 1982.

This invention relates generally to ophthalmology, but more particularly to an instrument for making both perforating and, especially, partial thickness accurately graded incisions in the cornea which is of particular import in the surgical treatment of myopia, astigmatism and certain other ocular conditions.

Parent Application No. 375272 discloses an instrument for making corneal incisions enabling such incisions to be made to a highly accurate graded depth. The instrument comprises a case provided with a holder of a cutting means, said holder being mounted reciprocately movable relative to the axis of said case by means of a drive provided with a micrometric screw. Positioned anteriorly to the holder adjacent the cutting means is a stop means for limiting the extent of movement of the cutting member of the cutting means, connected to the case, the stop means being adapted to abut on the corneal surface during surgery and serving as a guard controlling the cutting member insertion.

Although the above device significantly reduced complexity of the surgical protocol and increased operational accuracy, yet it failed to ensure reliable clasping of the cutting blade in a lock means provided in the form of a collet, thereby adversely affecting the surgical effect. Furthermore, the hitherto known design slowed down replacement of the cutting member leading to loss of the operational time.

It is an object of this invention to provide an instrument for making corneal incisions which can ensure reliable positioning of the cutting member or blade in the holder.

It is another object of this invention to improve the quality of surgical performance.

It is still another object of this invention to reduce the operational time requirement and enhance the surgeon's convenience while using the instrument for making incisions.

A main object of this invention lies in providing an instrument for making corneal incisions with a holder of a cutting means which can ensure positioning of a cutting member therein along with rendering the member easier to use.

The above and other objects of the invention are attained in an instrument for making corneal incisions, comprising a case with a holder of a cutting means being mounted therein for reciprocation relative thereto, said holder being provided with a drive for urging the latter in the axial direction, said drive having a lock means at one end thereof with its opposite end accommodating a spring-loaded stem for engagement with said drive, a stop means for limiting the extent of movement of the cutting member of said cutting means, being mounted anteriorly relative to said holder adjacent said cutting means, according to the invention, the section of the holder facing the stop means is rectangular in shape with the tip portion of said holder section having a rectangular-shaped groove adapted to receive a lever clip and forming, conjointly with the groove base, the lock means for said cutting means, and the case having a rectangular bore for this section of the holder to be movably accommodated therein.

An advantage of this invention reposes in that the rectangular configuration of the holder in cross-section reduces play during its movement, while the use of the lever clip greatly simplifies the surgeon's task and increases the reliability of holding the cutting member in position, all of the above factors being instrumental in enhancing the quality of surgical performance.

According to one embodiment of this invention, an instrument for making corneal incisions comprises a lever clip being essentially a section spring-loaded at the case end and terminating in a specially shaped portion at the opposite end whereby the cutting member is clasped securely in position.

The specially shaped portion may be fashioned into an involute curve whereby clasping of the cutting member in position is made even more efficient.

The invention also contemplates an instrument for making corneal incisions provided with an auxiliary groove arranged at right angles to the base of the clip groove and the auxiliary groove passing through the holder section for the purpose of removing foreign material penetrating into the clip groove whereby the routine of cleansing the instrument of foreign substance is substantially simplified.

In such an instrument for making corneal incisions the stop means is preferably flat and has a groove set in coplanar relation to the base of the groove of said lock means whereby the hazard of perforating the cornea is diminished.

The invention is further described by way of example only, with reference to the accompanying drawings, wherein.

Figure 1:
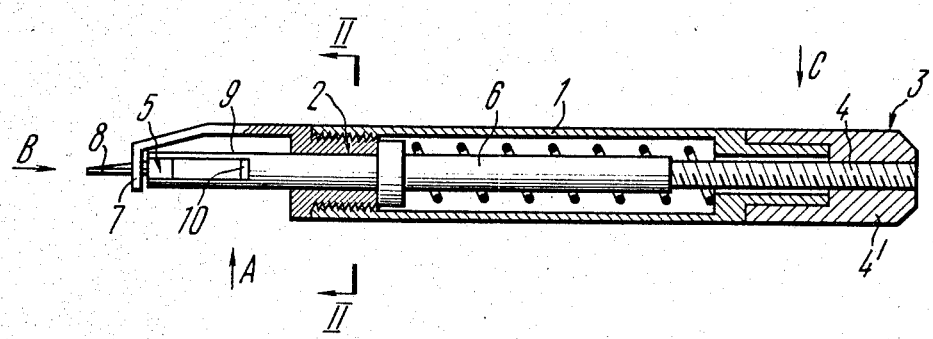
FIG. 1 shows the instrument for making corneal incisions, according to this invention, in section.

The instrument for making corneal incisions comprises a case 1 with a holder 2 of a cutting means being mounted therein for reciprocation relative thereto. The holder 2 is provided with a drive 3 made up of a screw 4 and a nut 4' for urging the holder 2 in the axial direction. The holder 2 has a lock means 5 at one end thereof, its opposite end having a spring-loaded stem 6 to be engaged by the drive 3. A stop means 7 for limiting the extent of movement of the cutting member of said cutting means 8 is mounted anteriorly relative to the holder 2 adjacent the cutting means.

Figure 3:
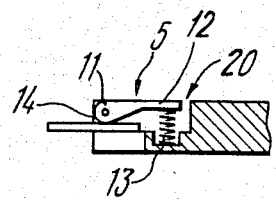
FIG. 3 is a view taken on line A of FIG. 1.
Figure 2:
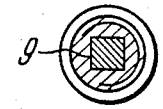
FIG. 2 is a sectional view taken on line II—II of FIG. 1.

FIG. 2 shows that a section of the holder 2 facing the stop means 7, is rectangular in shape when viewed in cross-section. As seen in FIGS. 1 and 3, the tip portion 9 of the holder section is provided with a rectangularly shaped groove 10 adapted to accommodate a lever clip 11 forming, conjointly with the groove base, the lock means 5 for cutting means 8. Auxiliary groove 20 is at right angles to the base of the clip groove and passes through the holder 2.

It will be seen in FIG. 3 that the lever clip 11 is essentially a member 12 spring-loaded by a spring 13. The member 12 terminates in a specially shaped portion 14 which is preferably formed as an involute curve.

Figure 4:
FIG. 4 is a view taken on line B of FIG. 1.

In FIG. 4 depicting a view along arrow B of FIG. 1, it can be seen that the stop means 7 is made flat and has a groove 15 arranged in coplanar relation to the base of the groove 10 of the lock means 5.

Figure 5:
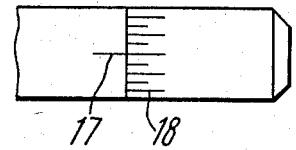
FIG. 5 is a view taken on line C of FIG. 1.

The drive 3 for reciprocating motion of the holder 2 is essentially a conventional pair made up of a screw and a nut and, therefore, is not dealt with in more detail as being impertinent to the subject of this invention. Suffice it to say that, as will be seen in FIG. 5, the holder can be set using a mark 17 and a scale 18 for the surgeon's convenience.

The instrument of this invention is operated as follows. The ophthalmosurgeon with his finger exerts pressure on the spring-loaded member 12 of the lever clip 11, and inserts a cutting tool into the gap formed between the specially shaped portion 14 and the groove 10. Clasping of the cutting member in position is effected by means of the shaped portion 14 with the help of the spring 13. Rotation of the drive results in the cutting tool being drawn into the groove 15 until it is set flush with the surface of the stop means 7. Position of the mark 17 is read on the scale 18.

Subsequent rotation of the drive 3 advances the cutting tool to given extent corresponding to the desired incision depth. The instrument is then used to perform the incisions with care taken that the stop means slides freely along the corneal surface, while the case 1 is held in position at right angles to the same.

The use of this invention will permit greater accuracy in making corneal incisions and substantially increase the surgeon's convenience.

We claim:

1. An instrument for making corneal incisions, said instrument comprising:
   a casing;
   a holding means slidingly mounted within said casing for reciprocative motion relative to said casing;
   a drive means for moving said holding means along the longitudinal axis of said casing;
   a locking means positioned at one end of said holding means to releasably lock a cutting blade;
   a spring means positioned at the other end of said holding means for biasing said holding means;
   a forked stop means defined by said casing to limit the movement of said locking means and to slide along a corneal surface, said forked stop means including two tongs and defining an opening between said two tongs to permit egress of said cutting blade;
   said locking means including a rectangular-shaped groove having a base defined by said holding means, said base of said rectangular-shaped groove being positioned parallel to a plane passing equidistantly between said two tongs of said forked stopping means;
   a spring-loaded lever clip mounted in said rectangular-shaped groove for biasing against the cutting blade; and
   a space defined between said spring-loaded lever clip and said base of said rectangular-shaped groove for receiving said cutting blade.

2. An instrument as claimed in claim 1, wherein said spring-loaded lever clip includes a member biased at an end against said holding member and defining an involute curved shape at an opposite end.

3. An instrument as claimed in claim 1, wherein said forked stop means is positioned perpendicular to the longitudinal axis of said casing and said opening of said forked stop means being coplanar with said base of said rectangular-shaped groove.

4. An instrument as claimed in claim 1, further comprising an auxiliary groove defined by said holding means for removing foreign material penetrating into said rectangular-shaped groove, said auxiliary groove being positioned perpendicular to said base of said rectangular-shaped groove.

5. An instrument as claimed in claim 1, wherein a portion of said holding means is rectangular in cross-section and a portion of said casing within which said portion of said holding means is slidingly mounted is of rectangular cross-section to reduce play of said holding means during movement.

* * * * *